(12) United States Patent
Krieger et al.

(10) Patent No.: US 10,089,737 B2
(45) Date of Patent: Oct. 2, 2018

(54) 3D CORRECTED IMAGING

(71) Applicant: Children's National Medical Center, Washington, DC (US)

(72) Inventors: Axel Krieger, Alexandria, VA (US); Peter C. W. Kim, Washington, DC (US); Ryan Decker, Baltimore, MD (US); Azad Shademan, Washington, DC (US)

(73) Assignee: Children's National Medical Center, Washington, DC (US)

( * ) Notice: Subject to any disclaimer, the term of this patent is extended or adjusted under 35 U.S.C. 154(b) by 383 days.

(21) Appl. No.: 14/555,126

(22) Filed: Nov. 26, 2014

(65) Prior Publication Data

US 2015/0145966 A1    May 28, 2015

Related U.S. Application Data

(60) Provisional application No. 61/909,604, filed on Nov. 27, 2013.

(51) Int. Cl.
*H04N 7/12* (2006.01)
*H04N 9/47* (2006.01)
(Continued)

(52) U.S. Cl.
CPC .......... *G06T 7/0051* (2013.01); *A61B 5/0075* (2013.01); *A61B 5/0077* (2013.01); *G06T 7/337* (2017.01); *G06T 17/20* (2013.01); *H04N 13/0018* (2013.01); *H04N 13/0203* (2013.01); *A61B 1/00193* (2013.01); *A61B 5/1079* (2013.01); *A61B 2034/2055* (2016.02); *A61B 2090/367* (2016.02); *A61B 2576/00* (2013.01); *G06T 2207/10004* (2013.01); *G06T 2207/10024* (2013.01); *G06T 2207/10052* (2013.01); *G06T 2207/20221* (2013.01); *H04N 13/0239* (2013.01); *H04N 13/0271* (2013.01); *H04N 13/239* (2018.05); *H04N 13/271* (2018.05); *H04N 2013/0074* (2013.01)

(58) Field of Classification Search
None
See application file for complete search history.

(56) References Cited

U.S. PATENT DOCUMENTS

| | | | |
|---|---|---|---|
| 8,891,006 B2 * | 11/2014 | Afshari | H04N 5/2257 348/340 |
| 2006/0043555 A1 * | 3/2006 | Liu | H01L 27/14618 257/680 |

(Continued)

FOREIGN PATENT DOCUMENTS

KR    10-2013-0060158 A    6/2013

OTHER PUBLICATIONS

International Search Report and Written Opinion dated Feb. 24, 2015 in PCT/US2014/067641 (with Search History).

(Continued)

*Primary Examiner* — Talha M Nawaz
(74) *Attorney, Agent, or Firm* — Oblon, McClelland, Maier & Neustadt, L.L.P.

(57) ABSTRACT

A system and method for corrected imaging including an optical camera that captures at least one optical image of an area of interest, a depth sensor that captures at least one depth map of the area of interest, and circuitry that correlates depth information of the at least one depth map to the at least one optical image to generate a depth image, corrects the at least one optical image by applying a model to address alteration in the respective at least one optical image, the model using information from the depth image, and outputs the corrected at least one optical image for display in 2D and/or as a 3D surface.

20 Claims, 15 Drawing Sheets

(51) Int. Cl.
  *H04N 7/18*     (2006.01)
  *G06T 7/00*     (2017.01)
  *H04N 13/00*    (2018.01)
  *G06T 17/20*    (2006.01)
  *A61B 5/00*     (2006.01)
  *G06T 7/33*     (2017.01)
  *H04N 13/02*    (2006.01)
  *H04N 13/239*   (2018.01)
  *H04N 13/271*   (2018.01)
  *A61B 1/00*     (2006.01)
  *A61B 5/107*    (2006.01)
  *A61B 90/00*    (2016.01)
  *A61B 34/20*    (2016.01)

(56) References Cited

U.S. PATENT DOCUMENTS

| | | | | |
|---|---|---|---|---|
| 2007/0021738 | A1* | 1/2007 | Hasser | A61B 8/12 606/1 |
| 2007/0060792 | A1* | 3/2007 | Draxinger | A61B 1/00009 600/117 |
| 2011/0285824 | A1* | 11/2011 | Bar-Zohar | G06T 7/593 348/46 |
| 2011/0285825 | A1* | 11/2011 | Tian | H04N 9/646 348/47 |
| 2012/0056982 | A1* | 3/2012 | Katz | G06F 3/017 348/43 |
| 2012/0200829 | A1* | 8/2012 | Bronstein | G02B 27/2271 353/7 |
| 2013/0251243 | A1* | 9/2013 | Shim | G06T 5/007 382/154 |
| 2013/0271757 | A1* | 10/2013 | Kang | A61B 3/102 356/300 |
| 2013/0296682 | A1* | 11/2013 | Clavin | A61B 6/5247 600/407 |
| 2014/0336461 | A1* | 11/2014 | Reiter | A61B 1/00193 600/111 |
| 2016/0278678 | A1* | 9/2016 | Valdes | A61B 5/14556 |
| 2016/0327779 | A1* | 11/2016 | Hillman | G02B 21/367 |

OTHER PUBLICATIONS

Extended European Search Report dated Jul. 27, 2017 in Patent Application No. 14865178.9.

* cited by examiner

3D CORRECTED IMAGING

CROSS REFERENCE TO RELATED APPLICATIONS

This disclosure claims the benefit of U.S. Provisional Application No. 61/909,604, filed on Nov. 27, 2013, the disclosure of which is incorporated herein by reference in its entirety.

BACKGROUND

Field of the Invention

The present embodiments are directed to a system and method of correcting undesirable abnormalities in acquired images through the use of 3-dimensional information and a distortion model.

Description of the Related Art

Image acquisition and post-processing are currently limited by the knowledge level of the user. Once captured, images have limited information to be used in correcting their defects. Some automated processing algorithms exist with defined goals that often misrepresent the underlying information. For example, the 'quick fix' touch up steps being developed by photo-sharing websites may change the saturation, gain, sharpness and other characteristics to make the resulting images more pleasing to the eye. The lack of additional information makes correcting complex artifacts and abnormalities in images difficult. Those image artifacts resulting from specular reflection, shadows, occlusion and other physical phenomenon are not able to be suitably corrected based on the information in a single camera image.

SUMMARY

With information about the geometry being imaged, one may be able to infer more about the underlying physical processes behind the more complex image distortions, and subsequently correct images to show the underlying objects most clearly. With the ability to sense depth, an optical imager can determine much more about its environment. This knowledge, combined with knowledge of the camera and light source used in a scene, opens new possibilities for post-acquisition image correction.

The light source in a scene is of key importance in evaluating and correcting for optical distortions. Specular reflection, shadows, and diffuse reflection depend on the position and intensity of illumination. Some information about the position and intensity of the light source can be inferred with knowledge of the 3D surface and location of specular reflections and shadows. But distance between the imaged object and light source is much harder to estimate. With prior knowledge of the light source position, one could more accurately model the physical phenomenon contributing to image distortion and correct for additional situations and additional types of illuminating radiation.

With the ability to sense depth, a camera could better inform a variety of post-processing algorithms adjusting the content of an image for a variety of purposes. For example, a face may be illuminated evenly post-capture, even in the event of severe shadows. A body of water and what lies beneath could be better understood even in the case of large specular reflections. An astronomy image can be better interpreted with knowledge of the terrestrial depth map. More generally, increased information about the physical world an image is captured within, including the subject to be imaged, will better inform automatic approaches to increasing the image quality by correcting for distortions that have a physical basis in reality. This information could be used to correct for object occlusion, shadows, reflections, and other undesired image artifacts. Such an approach offers many advantages to the medical community and others who desire maximal information from images for the purposes of image analysis.

In addition to the qualitative improvements in image quality, 3D corrected imaging offers many advantages to an image analysis pipeline which relies on quantitative methods to extract information about underlying structures and details in images of interest. One major application of this quantitative analysis is in the field of medical imaging, where diseases and abnormalities are often quantified, categorized, and analyzed in terms of their risk to the patient. A more robust approach to assess these conditions will help level the playing field and allow non-experts to make informed decisions regarding patient diagnosis. In addition to the information obtained from depth maps, additional insight can be gained through the use of multispectral or hyperspectral imaging. This will enable the observation and segmentation of previously obscured features, including blood vessels and wavelength-specific contrast agents.

Medical imaging can be a subjective field. Often, experts are not completely sure about the underlying physical explanations for perceived abnormalities or features observed in acquired images. The possibility of better image visualization has led to the adoption of 3-dimensional technologies such as magnetic resonance imaging (MRI) and x-ray computed tomography (CT) and their use in medical imaging. Optically acquired images, however, still suffer from a lack of depth information and sensitivity to distortion, as well as image artifacts and reflections.

Since optical images are an easily obtained, low-risk modality which can be used in real-time intraoperatively, it would be useful to improve the accuracy of these types of images. This will enable those analyzing the images to better understand the underlying physical phenomena, more readily identify abnormal growths or function, more easily communicate these observations to those without experience in medical image analysis, and to have greater confidence in treatment plans based on the acquired medical images.

One approach to better understand optical images is to "flatten" the image of a 3D object onto a plane for further analysis. Most previous applications of this idea have been in the domain of computer graphics. For instance, U.S. Pat. No. 8,248,417 (incorporated herein by reference) discloses a computer-implemented method for flattening 3D images, using a plurality of polygons divided into patches. This is for the purpose of applying 2D texture maps to 3D surfaces. Many such applications are of this "forward projection" type, where a generated 2D image is draped over the 3D surface. Further, U.S. Pat. Pub. No. 20110142306 (incorporated herein by reference) discloses the flattening of 3D medical images for the purpose of determining myocardial wall thickness.

The use of optical cameras allows real-time imaging without concern for radiation. The proliferation of laparoscopic tools, such as is described in U.S. Pat. No. 20110306832 (incorporated herein by reference), allows small imagers to be used inside the body and manipulated with dexterity. Previous applications of 3D flattening were mostly concerned with the projection of flat, pre-rendered textures onto a deformed 3D surface. The disclosed embodiments regard the opposite intent. That is, a system and method to accurately flatten the existing textures and optical information from 3D surfaces with minimal distortion and maximal information retention. Subsequently one may use information from the 3D depth map to correct abnormalities in the optical image. These flattened, corrected images may then be overlaid on the 3D image for visualization purposes, or used to provide corrected 2D images.

The present embodiments provide a system and method to correct 3D images for undesirable artifacts, including reflections.

According to one embodiment, the system comprises a camera, which may be configured for spectral sensing, to obtain images of the area of interest, a distortion model to predict the degree of image distortion due to reflection or other physical phenomena, and 3-dimensional spatial information obtained from a light-field camera or other suitable 3D camera arrangement. According to one embodiment there is described a method for registering the optical image data with the 3D spatial information. According to one embodiment there is described a method to correct for undesired image distortion or artifacts which is informed by the 3D depth information and other knowledge of the camera arrangement and physical environment. According to one embodiment there is described a method for determining the possible deformations of the 3D image data, satisfying a multitude of relevant parameters designed to minimize the loss of relevant information.

The method includes an automatic or manual processing step where the desired distortion correction is weighed against the possible deformations of the 3D image data and an output preview which may include a variety of options for displaying the distortion-corrected image on a 3D model. According to one embodiment there is described a method to suggest camera and illuminating light positions, orientations, parameters, and model types based on previous images, optimized to minimize distortions and artifacts in regions of interest and a device to display the corrected image data.

A further understanding of the functional and advantageous aspects of the invention can be realized by reference to the following detailed description and drawings.

DETAILED DESCRIPTION

Figure 1:
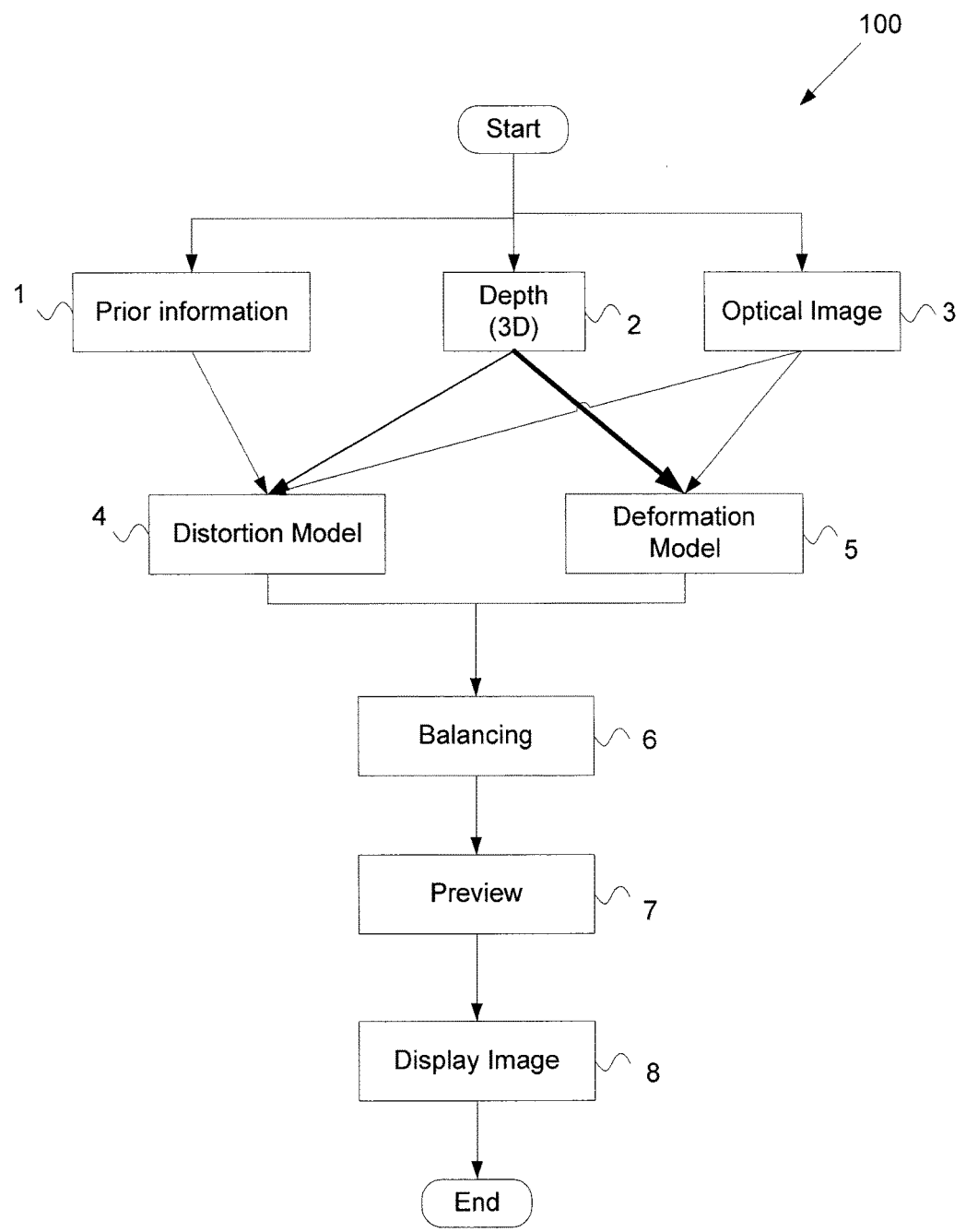
FIG. 1 illustrates procedural flow to generate a corrected 3D image.

In the drawings, like reference numerals designate identical or corresponding parts throughout the several views. Further, as used herein, the words "a", "an" and the like generally carry a meaning of "one or more", unless stated otherwise. The drawings are generally drawn to scale unless specified otherwise or illustrating schematic structures or flowcharts.

Furthermore, the terms "approximately," "proximate," "minor," and similar terms generally refer to ranges that include the identified value within a margin of 20%, 10%, 5% or greater than 0%, and any values therebetween.

Without limitation, the majority of the systems described herein are directed to the acquisition and analysis of medical images. As required, embodiments of medical imaging systems are disclosed herein. However, the disclosed embodiments are merely exemplary, and it should be understood that the disclosure may be embodied in many various and alternative forms. The systems and methods described herein may be applicable to any image acquired with any camera.

The figures are not to scale and some features may be exaggerated or minimized to show details of particular elements while related elements may have been eliminated to prevent obscuring novel aspects. Therefore, specific structural and functional details disclosed herein are not to be interpreted as limiting but merely as a basis for the claims and as a representative basis for teaching one skilled in the art to variously employ the present embodiments. For purposes of teaching and not limitation, the illustrated embodiments are directed to 3D corrected imaging.

Figure 9:
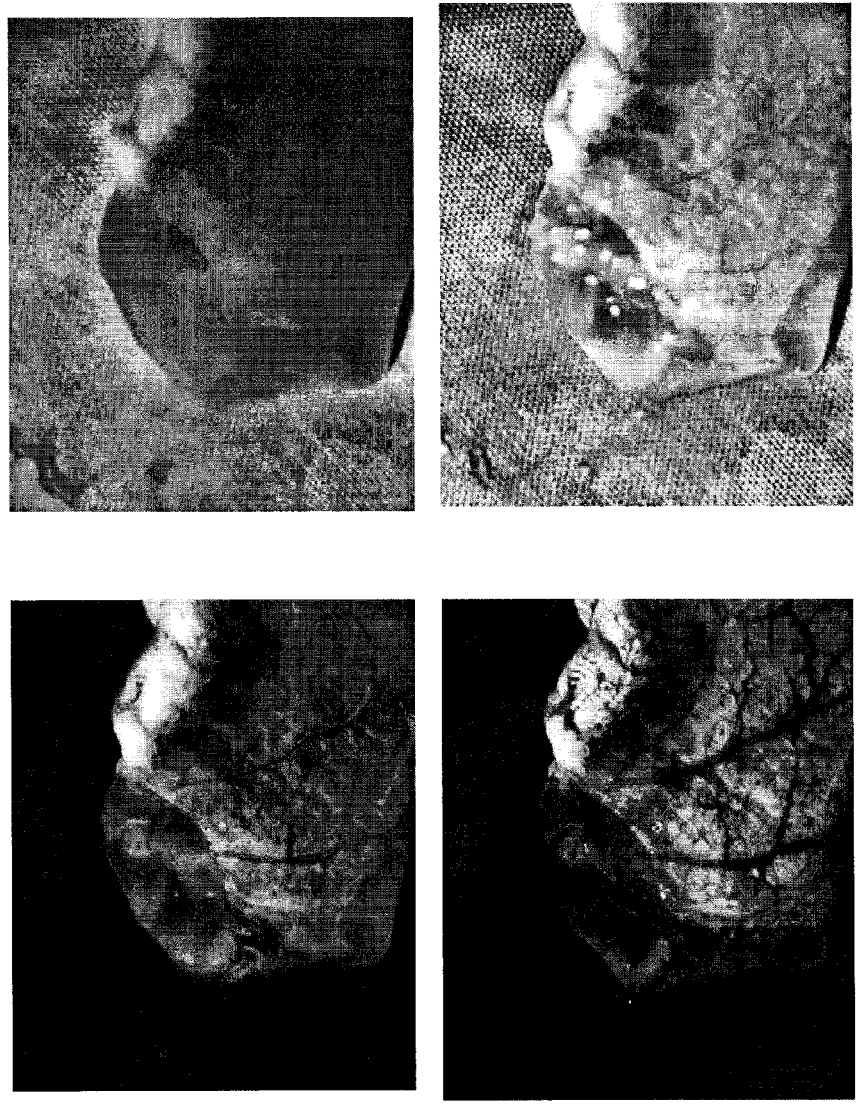
FIG. 9 illustrates the potential benefits from multispectral imaging.
Figure 13:
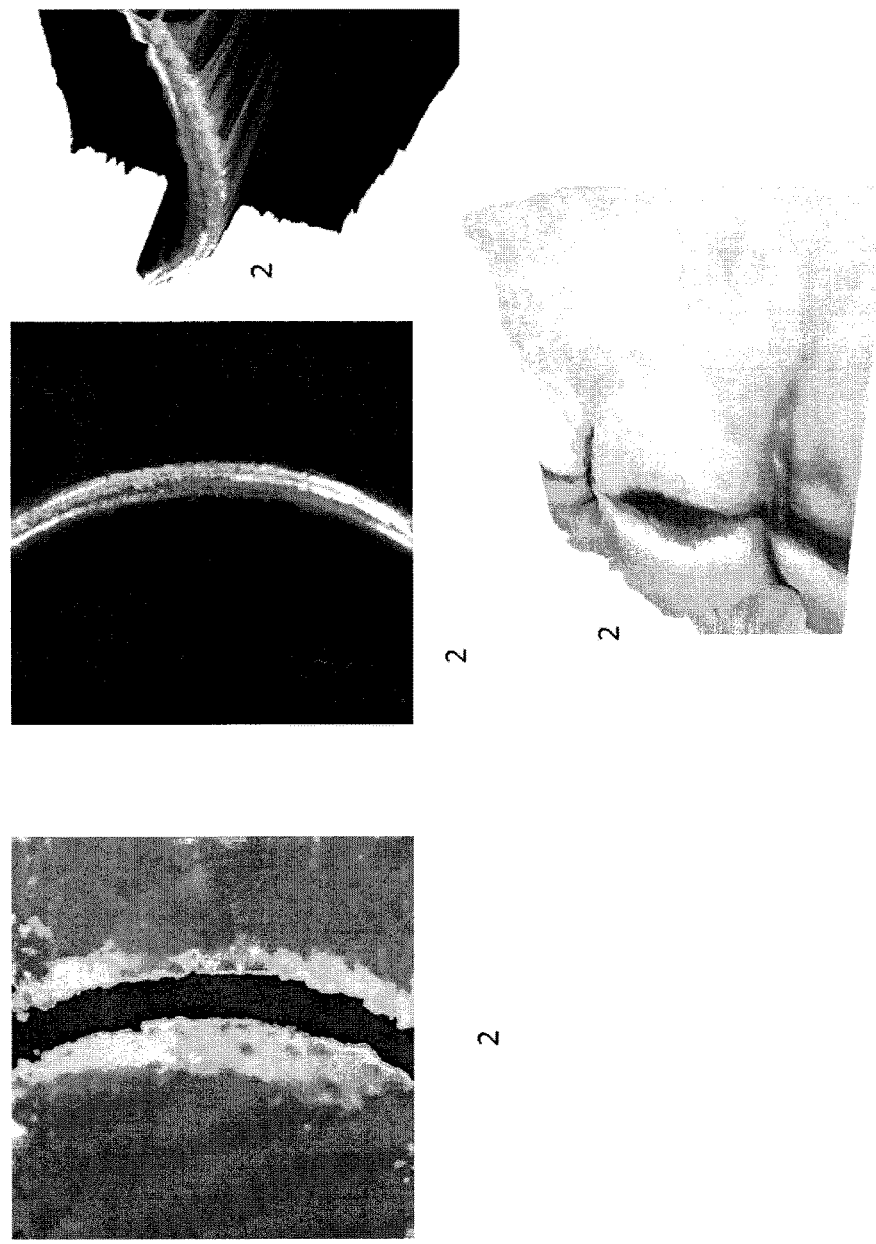
FIG. 13 illustrates image from a capable depth sensing circuitry, in this case a 3D light-field camera.

The flowchart in FIG. 1 shows an exemplary procedural workflow to perform the imaging corrections. The process can be performed when an object and an imaging system are in place. An optical image 3 is acquired along with a depth map 2 over at least a portion of a field-of-view (FOV). Information can be inferred from the optical image 3 such as areas of specular reflection, color information and transform-invariant features. Information about the depth of corresponding optical image 3 pixels can be determined based on their position in the depth map 2, which can be obtained from a 3D-capable depth sensor. Example images developed from optical image 3 and depth map 2 are shown in FIGS. 9 and 13. FIG. 9 illustrates the images possible with multispectral imaging in tissue. The use of multispectral imaging allows the imaging system to focus on specific features which are better seen at different wavelengths of light, and combine these images to form a more complete overview of the object. FIG. 13 presents exemplary depth images 2 obtained from a light-field camera that would provide information about the 3D structure of the object of interest.

In addition to optical image 3 and depth map 2 information, prior information 1 such as tissue properties, light polarization, wavelength and electromagnetic field properties, is also input to the imaging system. Prior information 1 also includes camera parameters, light source information, and depth sensing mean information. Camera parameters may include focal length, FOV measurements, exposure, and other intrinsic or extrinsic camera parameters. Prior information 1 may include information relevant to the projected reflection distortion, such as the intensity and directionality of illumination, material composition, wavelength, polarization, electric and magnetic fields. Prior information 1 may also include information obtained from prior images or relevant image databases. These three sources of information converge to generate an image distortion model 4, where the distortion is caused due to the imaging system.

The distortion model 4 serves a dual purpose of informing the overall process of the goals for image correction and providing a physical basis for the desired image corrections. The distortion model 4 can be used to adjust the lighting in a scene after image acquisition with realistic outcomes. Both the optical and 3D images previously acquired also send information to a separate algorithm, the deformation model 5, which is responsible for assessing the deformations to apply to the 2D images to achieve a 3D representation.

The distortion model 4 calculates the projected distortion and location of image artifacts based on current physical models of image acquisition and reflectance. The distortion model 4 uses the optical and depth image along with the prior information 1. The distortion model 4 includes a 2D image with depth at each pixel, giving a 3D surface at which each pixel contains additional information relevant to the correction of imaging abnormalities such as amount of extra light due to reflection, adjustment in illumination due to surface orientation and occlusion, expected radiance and diffusion due to surface roughness and other material properties, such as irregularities in color inferred from adjacent areas. These are sensitive to the position and intensity of the light which must be known at the time of image acquisition. This is accomplished by an encoded or tracked light source and a model of the light source, which may be a point or extended model. The distortion and deformation models are dynamic in nature and updatable over time as the user gains a better understanding of the specific underlying processes affecting image acquisition and quality in the particular context. One easily understood physical model is used to calculate the reflection from a surface. Knowing the surface orientation, which may be represented as a vector normal to a patch of the surface, and the angle of incoming light, the angle of reflected light can be predicted according to the law of reflection. The fundamental law of reflection states that the angle of incident light is equal to the angle of reflected light measured with respect to the surface normal (for instance, $\theta_i = \theta_r$ described below). A more complicated case may arise when tissue with varying optical properties is used, absorbing or allowing transmission of some light and reflection of other amounts. In this case, the specular-only reflectance model is not fully accurate, and must be updated to include mechanisms of diffuse reflection. For example, the distortion model may incorporate more advanced lighting models such as the Oren-Nayar model, which takes into account the roughness of a surface. In many cases the assumption that a surface appears equally bright from all viewing angles (Lambertian surface) is false, such a surface would be required to calculate the distortion model radiance according to the Oren-Nayar or similar model. In one embodiment, the Oren-Nayar model takes the following form:

$$\text{ReflectedLight} = (\rho/\pi) * \cos(\theta_i) * (A + (B * \max[0, \cos(\theta_i - \theta_r)] * \sin(\alpha) * \tan(\beta)) * E_o$$

where,
$\theta_i$ is an angle of incidence of light
$\theta_r$ is an angle of reflection of light
$\rho$ is a reflection coefficient of a surface,
A and B are constants determined by a surface roughness,
$\alpha$ is a maximum of the angles of incidence and reflection,
$\beta$ is a minimum of the angles of incidence and reflection,
$E_o$ is the irradiance when the surface is illuminated head-on.

In the case of a perfectly smooth surface, A=1 and B=0 and the equation reduces to the Lambertian model as:

$$\text{ReflectedLight} = (\rho/\pi) * \cos(\theta_i) * E_o$$

$E_o$ is determined first for the area of interest containing no objects. In this case the light illuminates a flat white surface head on and uses this information in subsequent steps for normalization of illumination. Also during this time it may be appropriate to calibrate the internal parameters of the optical and/or depth camera with a calibration procedure, typically utilizing a reference pattern or object to tease out distortions due to the cameras themselves. Calibration must also quantify the reflected light across the camera view under reference conditions, achieved by shining the light source perpendicular to a highly reflective, homogeneous surface. This can then be used to normalize reflected light while capturing subsequent images at the same light source location. The calibration step is necessary once to inform the intrinsic parameters used in the prior information that informs the distortion model. The combination of this prior information and sensory information can then be used to correct for undesired effects. For example, one factor in the distortion model, which can be assessed with knowledge of the 3D surface and lighting conditions, is occlusion. If a region is occluded, the region will appear darker due to shadows and have limited depth information. The distortion model recognizes such areas, knowing the lighting conditions and 3D surface, and will be used to generate possible surface features by interpolating characteristics of the surrounding unclouded area such as color, texture, and 3D surface information. Another example using the distortion model is the case of specular reflections. Again with knowledge of the lighting conditions and 3D surface information, reflections can be predicted according to material properties. These predictions from the distortion model can be compared with the observed imaging subject and used to smartly reduce the negative effects of specular reflection, namely loss of underlying information through an interpolation of the surrounding clear areas, selective adjustment of image post-processing parameters restricted to affected regions, or a combination of both. Combining different embodiments of the distortion model approach allows the imaging subject to be better understood even with biases due to imaging or subject irregularities. It is even possible to correct for specular reflection without knowledge of the lighting conditions by capturing multiple images at different lighting angles and performing a data-dependent rotation of the color space. One exemplary use of the distortion model is using the optical properties of the imager to predict and correct for distortion due to the intrinsic camera parameters like focal length, principle point, skew coefficient, lens arrangement etc. For example, fisheye or barrel distortions are example of effects caused due to intrinsic camera parameters. Such distortion correction only requires prior information and no knowledge of the depth map or optical image.

Figure 11:
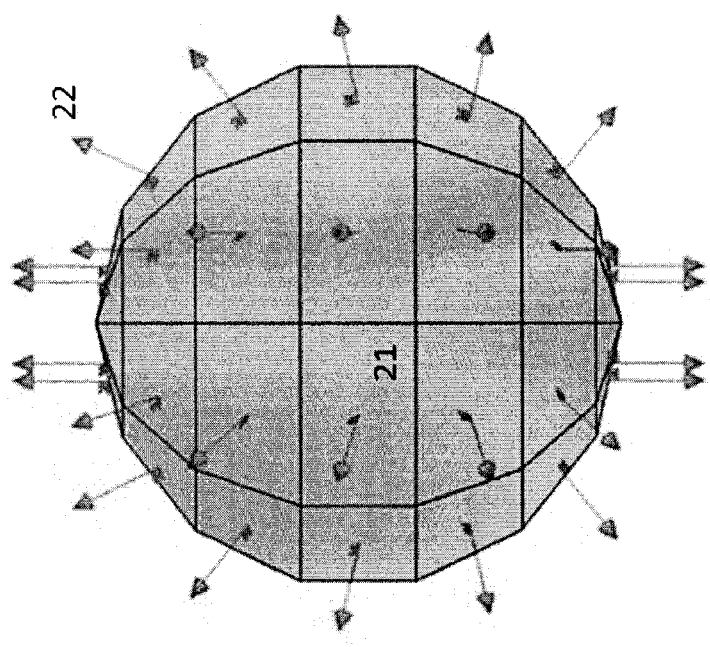
FIG. 11 illustrates exemplary polygon generation with normal vectors on a sample sphere.
Figure 12:
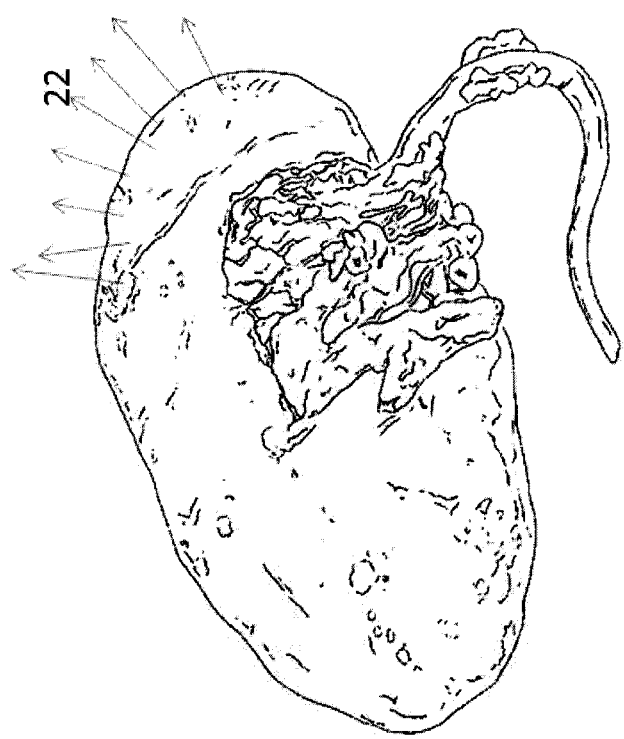
FIG. 12 illustrates the polygon normal vector generation on a realistic organ.

A deformation model 5, which uses the depth map and optical image but no prior information, breaks the joined optical image 3 and 3D image into a multitude of polygons (see example polygon 21 in FIG. 11) with known size and orientation, which may be grouped into discrete islands or patches. This information comes mainly from the 3D image obtained by a 3D camera, although there are techniques to further inform the deformation model 5 such as shape-from-shadow, monocular depth cues such as occlusion or relative size, or movement-produced cues in images obtained from the 2D optical imager. The deformation model 5 may be tuned to accommodate various desired characteristics, such polygon size, deformed polygon transformation metrics, minimal deformation of certain regions, and minimization of total patch curvature. The size of the polygons is inherently related to the curvature of the region which it represents. FIG. 11 illustrates the polygon 21 generation on an exemplary surface, including the normal vectors 22. FIG. 12 illustrates this normal vector 22 generation on a more relevant surface, which used for illustration in different figures in the embodiments of present disclosure.

The deformation model 5 places polygons (see example polygons 21 in FIG. 11) in accordance with model parameters, typically to minimize the overall curvature of the resulting mesh. Where areas of high curvature are encountered, the mesh algorithm may choose to separate patches comprised of a multitude of polygons and deform these separately. The centroids of these patches are areas with relatively low curvature. The centroids may be manually placed or adjusted according to the desired features to be observed in the image. The deformation model 5 is constantly updated to include new information gained from the depth-sensing circuitry. In the case of the laparoscopic embodiment, discussed later, the constant updating allows for the computer workstation to keep a relatively local, up-to-date 3D model of the environment which is in the FOV. This can be useful not only for the image correction applications, but also for intraoperative navigation of other tools.

The output from the distortion model 4, the predicted distortion due to image acquisition, is reconciled with the deformation model output according to the 3D structure of the tissue sample in a balancing step 6. This balancing step takes the 2D images with additional pixel information that are the result of the deformation and distortion modeling, and uses the combination of the two to adjust post-processing image parameters to account not only for the distortion caused by imaging abnormalities, but also by image artifacts caused by the imaging of a 3D deformed surface. Areas with high degrees of relevant predicted distortion, such as specular reflection, are assessed in terms of their ability to be corrected with prior information or additional information in the optical and depth image 2. For example, if there is an area with an image artifact, the surrounding areas of acceptable quality may be extrapolated or interpolated in order to approximate the optical image 3 at the distorted region. These extrapolations or interpolations would be better informed if the sampled regions were of similar angles to the distorted region. In another case, if there is an area with dark shadows, the angles and locations of these regions may be calculated relative to the illuminating source model, and their gains may be adjusted to more closely match an evenly illuminated object. In another case, a pinhole camera model may produce an undesirable non-uniform scale, where closer objects appear larger than those farther away. With the information from a light field camera or other depth-sensing circuitry, not only can the perspective of an optical camera be adjusted post-acquisition, but the entire pinhole camera model can be changed to a parallel model, representing objects with a uniform scale at every depth. This may be useful for feature size comparison across the depth FOV. In many cases, the reconciliation of the distortion and deformation model may be done automatically by weighting the confidence in their respective parameters, and satisfying a cost function which prefers a certain balance between information from both models. In more special cases, a human operator may be involved in assessing the performance of different amounts of image correction by adjusting the contribution of these models and observing the results as they are displayed on an image.

The result of the balancing processing step 6 is one or a plurality of images which minimize the image distortion and satisfy a plurality of input conditions corresponding to the deformation model 5 parameters. These images are then previewed in step 7 and displayed in step 8, with minimized distortion artifacts and uniform lighting. If uniform lighting is not desired, the user has the option to locate a virtual light for illumination of the 2D and/or 3D image.

Medical image analysis is concerned with separating normal tissue patterns and biological systems with abnormalities or malfunctioning systems. The complexities of the human body and inherent variability between patients make quantitative patterns difficult to implement in an image analysis system. However, the conditions of the physical world and optical parameters of an imaging system may be used to predict distortions during the capture of medical images for subsequent image correction. These images may be deformed in 3 dimensions and/or processed by other techniques to reduce the predicted image distortion due to reflection and other physical processes. This will enable the physician to better distinguish abnormalities due to underlying biological problems from abnormalities due to imperfect image acquisition. For example, a strange shadow can mistakenly be interpreted as a cancerous region. With knowledge of the angles of surrounding tissue and the position and behavior of the light source, shadows due to uneven lighting can be separated from those due to physical abnormalities. With multispectral imaging, features such as vessels can be more easily identified. It would be very useful to provide a vasculature map in 3D using the easily segmented vessels from multispectral imaging combined with the depth map generated by a light-field camera. This advantage is provided by the present embodiments.

Figure 10:
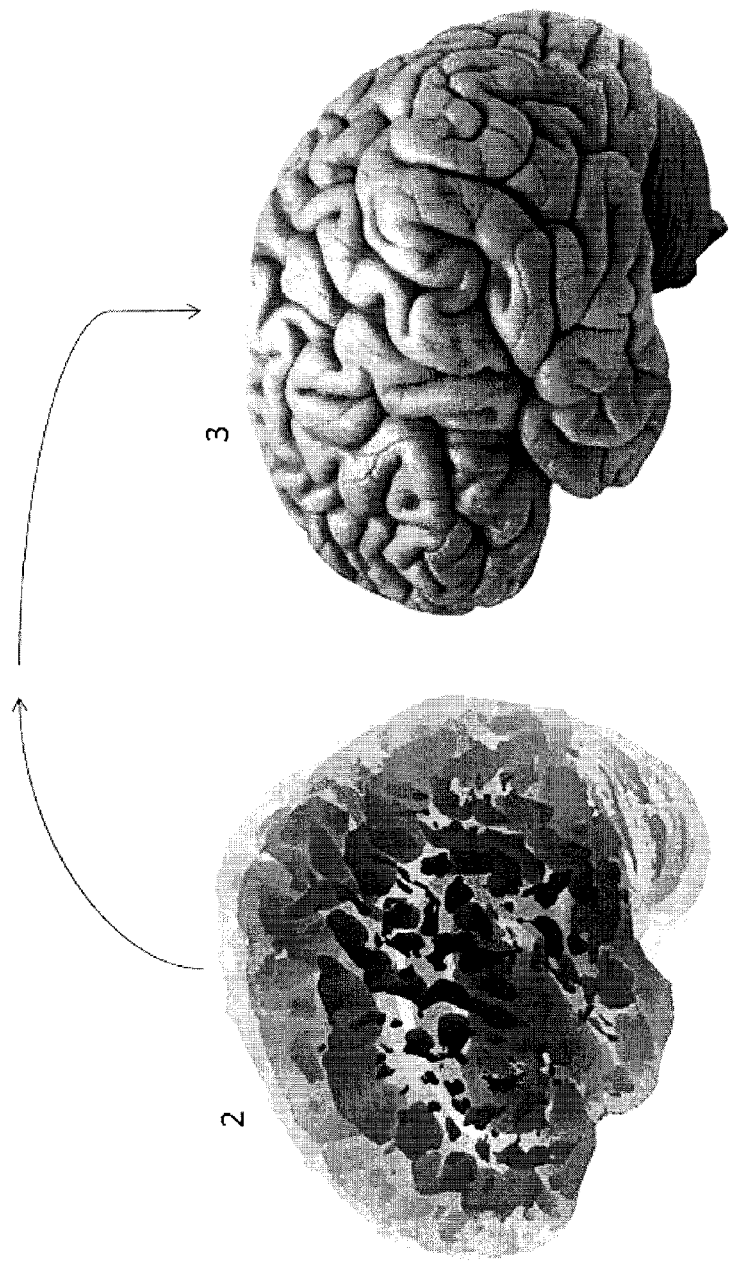
FIG. 10 illustrates a depth map to optical image registration.

The fusion of multispectral and light-field technology brings benefits that the technologies cannot provide separately. The principle of light-field depth perception is based on a low-level image registration between many small micro-lenses. This registration is based on the matching of features in slightly disparate views seen by each micro-lens. FIG. 10 illustrates the registration between a depth map 2 and optical image 3. The depth map 2 and optical image 3, which are obtained during the processes in FIG. 1 or 3, may be registered to one another with knowledge of the camera positions and orientations. If a particular band of frequencies would enhance contrast of a selected set of features in an imaged object, then the depth of those features could be more easily and robustly determined by the light-field camera with a particular multispectral filter. This could help provide more selective, highly accurate depth maps for certain objects of interest. For example, detailed maps of vasculature surrounding a cancerous region can be captured simply by imaging the tumor.

Figure 2:
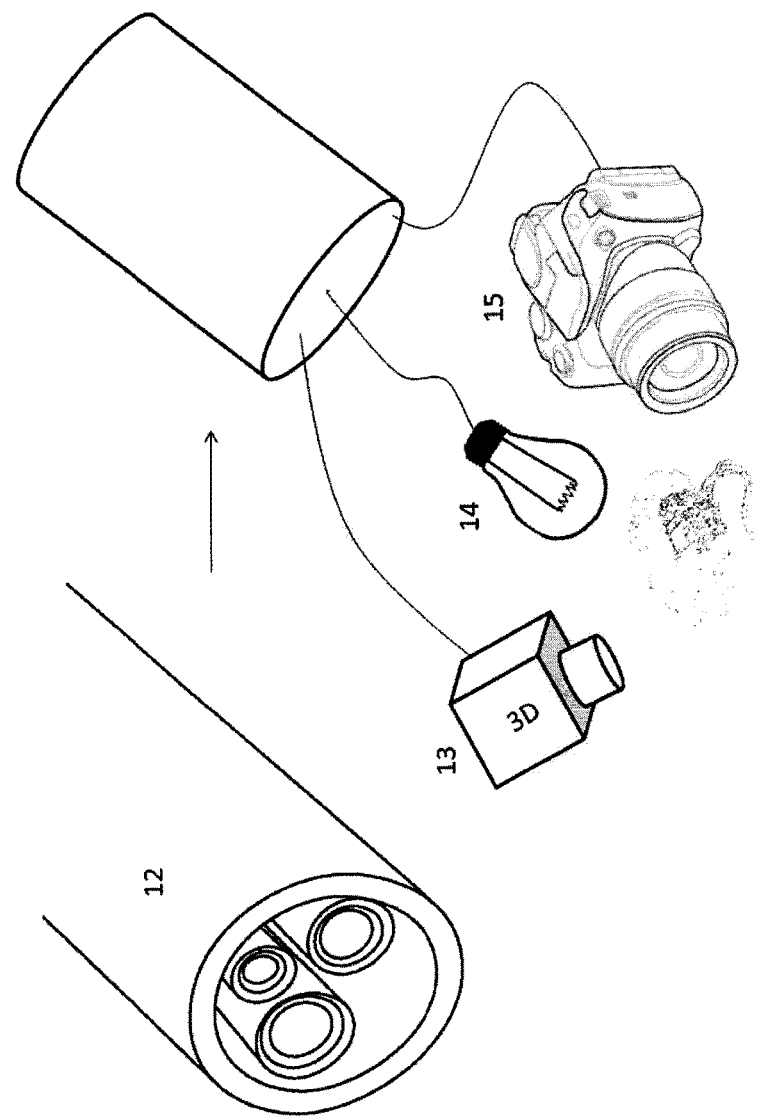
FIG. 2 illustrates an exemplary embodiment where optical and light-field cameras are mounted to a laparoscopic tool, shown in closed and open form.

In one embodiment, shown in FIG. 2, an exemplary imaging system is implemented in a laparoscope 12 that contains a 3D camera 13, a light source 14, and an optical camera 15 directed at an interesting object. The optical camera 15 may be a multispectral camera for image acquisition that captures several images at discrete and narrow bands of electromagnetic spectrum and the 3D camera may be a light-field camera for depth information. The images from these cameras are fed to a computer workstation and monitor (such as the computing device shown in FIG. 14), which the surgeon may operate via convenient human interaction methods. The use of a light-field camera is new to the field of medical imaging, as many systems rely on optical or electromagnetic trackers to obtain depth information. In a tracker-marker system, an object whose position and orientation must be traced is equipped with markers. There are different types of markers. For example a marker could be a light reflector or emitter, which can be tracked using a camera configured to scan and detect the marker. A marker could be a transmitter which transmits electric or magnetic field, which can be tracked using an electronic system configured to detect the transmitted filed. A marker could also be a dye which can be tracked by a scanner such as a computed tomographic (CT) scanner.

The light field camera has the advantage of directly computing the depth of each pixel in a captured image, as opposed to only the tracked markers of optical and electromagnetic trackers. It is also more reliable than a multi-camera arrangement for certain types of features and objects, where the multi-camera arrangement may be unable to match images from disparate views for certain surfaces, particularly highly and irregularly curved objects. The laparoscope 12 also has an illuminating light 14 which may be moved to varying positions depending on the requirements of the desired images. The system includes one or more optical cameras 15, which may be configured for multispectral imaging. The FOV of these cameras overlaps at least partially with the FOV of a depth-sensing camera or camera arrangement. In this manner, image fusion allows images obtained through the multispectral or other optical cameras 15 to be adjusted using the information from the 3D depth-sensing camera 13, and information shared and overlaid between modalities.

In another embodiment, a low-cost depth sensor is commonly available for smartphones and other consumer cameras. With the acquired optical image, a depth map 2 (in FIG. 1) is also taken. This map can then be used for a variety of purposes. For example, it can quickly and robustly detect and identify faces in the image. These regions can then be adjusted for optimal illumination and detail. Another use may be to guide the user to a different location for a better picture of a landmark with occlusions. In these cases, the output would be a corrected 2D image, and the 3D information would only be used in the processing stages.

In another embodiment, these images may not be previewed by the operator, and a decision may be made either manually or automatically as to whether the image is acceptable based on the input criteria. If it is acceptable, the final rendering of the deformed medical image is displayed, including multiple corrections for image distortion, artifacts and reflection.

Figure 3:
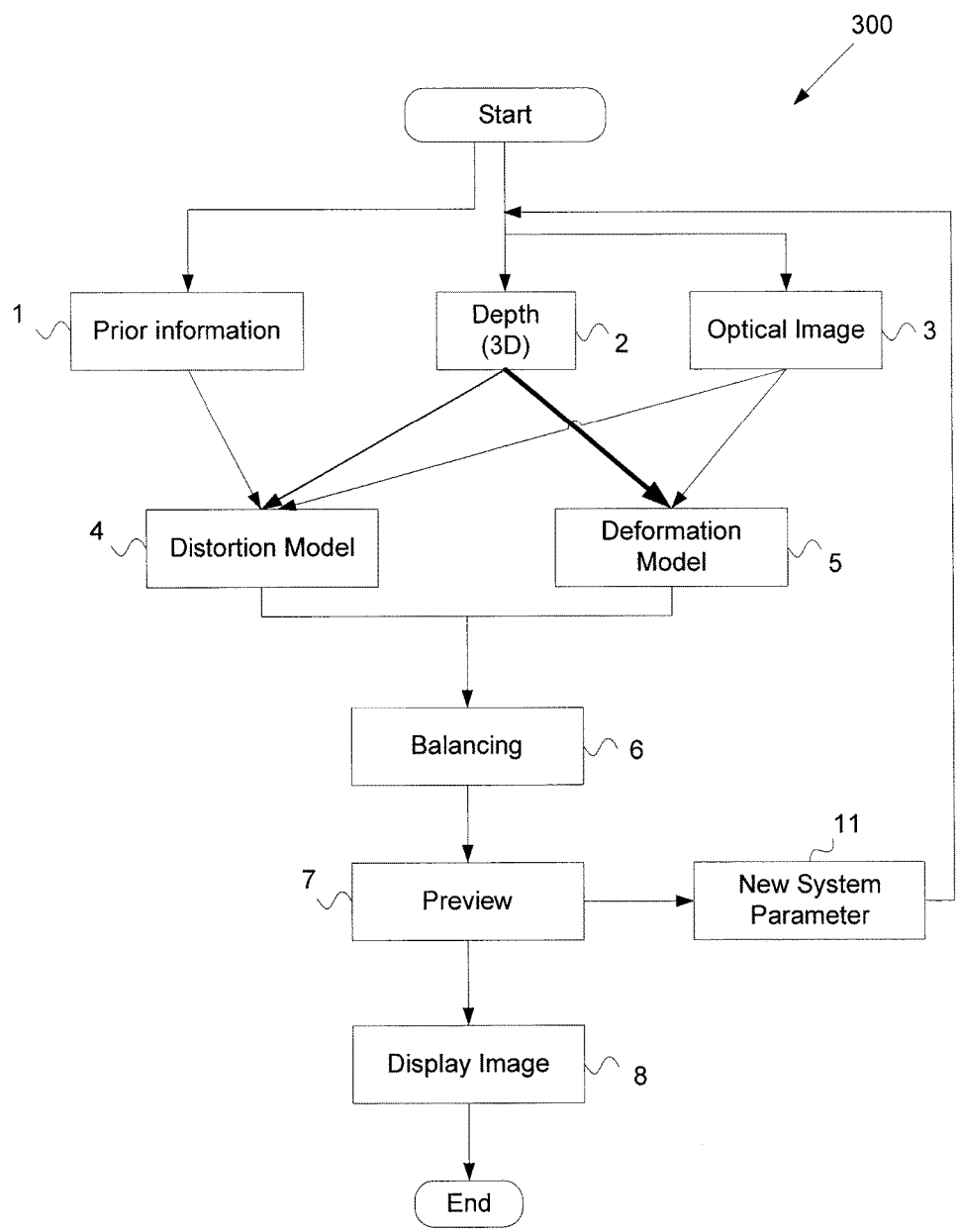
FIG. 3 illustrates an alternate procedural flow with an additional iterative step taken to generate a corrected 3D image.

FIG. 3 is an alternate exemplary process of image correction and similar to the process in FIG. 1. One difference is that, in FIG. 3, after the preview step 7, a feedback loop is provided which includes a new system parameter determination step 11. The previewed image, in step 7, may be deemed unacceptable for the application. In this case, the system may use information about the camera parameters and imaged object to determine a new set of system parameters 11 which will yield a more accurate image of the desired region. For example, if a portion of the corrected 3D image is impossible to recover because of shadows or occlusion, then the system may suggest moving the light source 14 (in FIG. 2) or camera position. The computer workstation may take into account the current configuration, yielded images, and object geometry, and make a suggestion to change any or all of the following: optical image-sensing circuitry, depth-sensing circuitry, camera or depth sensing sensor position, camera or depth-sensor orientation. Alternatively, if the image is acceptable, the system may still suggest new positions and orientations for the camera and depth-sensing circuitry if the user desires a planned image path, or a FOV which is not fully captured in one acquisition sequence. This step of acquiring new images using computer-suggested system parameters 11 may be iterated to improve image quality further or to guide a planned study.

Figure 4:
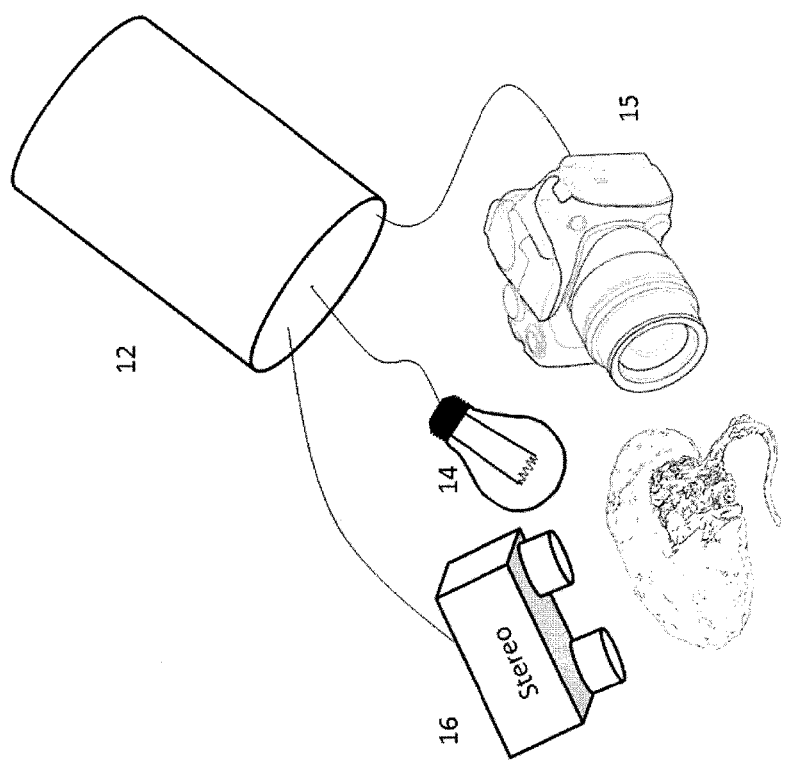
FIG. 4 illustrates another embodiment where the laparoscopic tool includes a stereoscopic camera arrangement for depth-sensing.

In another embodiment, shown in FIG. 4, the imaging system is comprised of an endoscope, with an optical camera 15 and a stereo vision camera 16. The stereo vision camera has at least two cameras are arranged relative to each other such that images of an object can be captured from different viewpoints. These images are then processed to extract 3D information pertaining to an object. The increased physical separation between different cameras will lead to an improved 3D depth perception than that of the close mounted dual cameras in existing systems. The increased number of cameras (preferably three or more) present in the disclosed invention will lead to enhanced visualization of the anatomy through image stitching. The baseline 17 between 2 or more cameras may be adjusted to suit the application and desired performance characteristics.

In another embodiment, the depth sensing circuitry may use structured light. In this case a separate light projects a grid or other known geometry onto the imaging subject, and a camera processing algorithm computes the depth in the field of view from the distortions in this known geometry.

Figure 5:
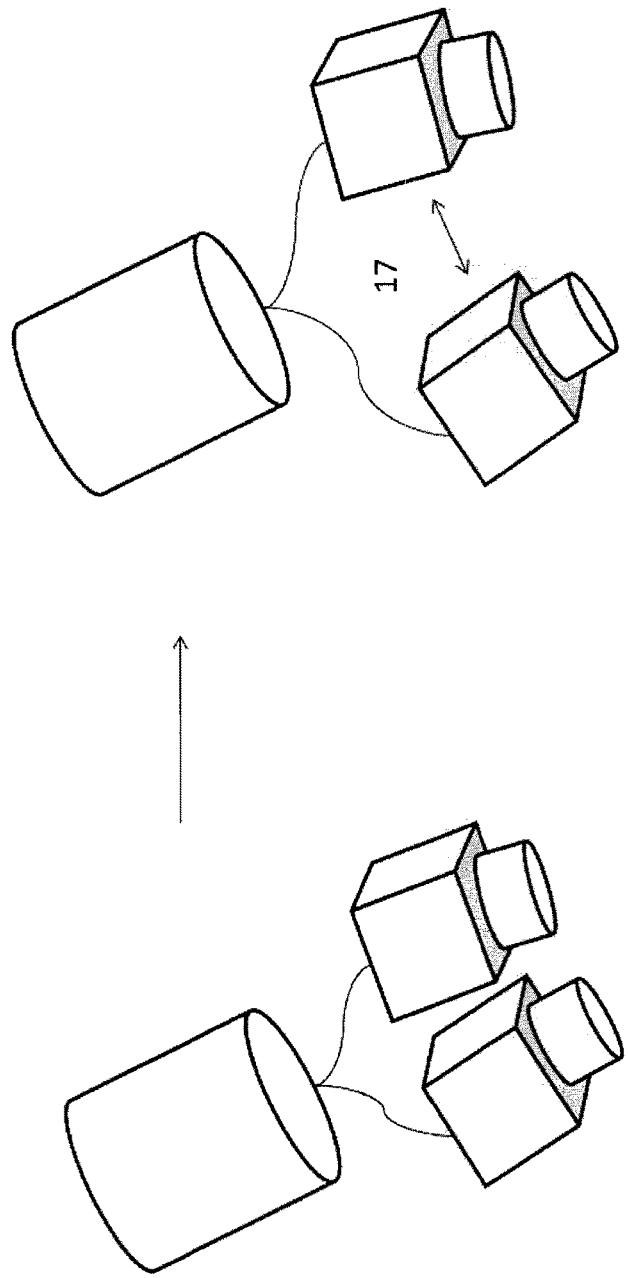
FIG. 5 illustrates another embodiment where the cameras are used externally.

In another embodiment, the laparoscopic tool 12 (in FIG. 2) may have a plurality of cameras which are configured for stereo vision via a beam splitter, which is a device that splits a beam of light into two. This allows a larger variety and number of cameras in a smaller space, which is ideal for laparoscopic configurations. FIG. 5 illustrates the extension of the baseline 17 of a stereoscopic camera 16.

Figure 6:
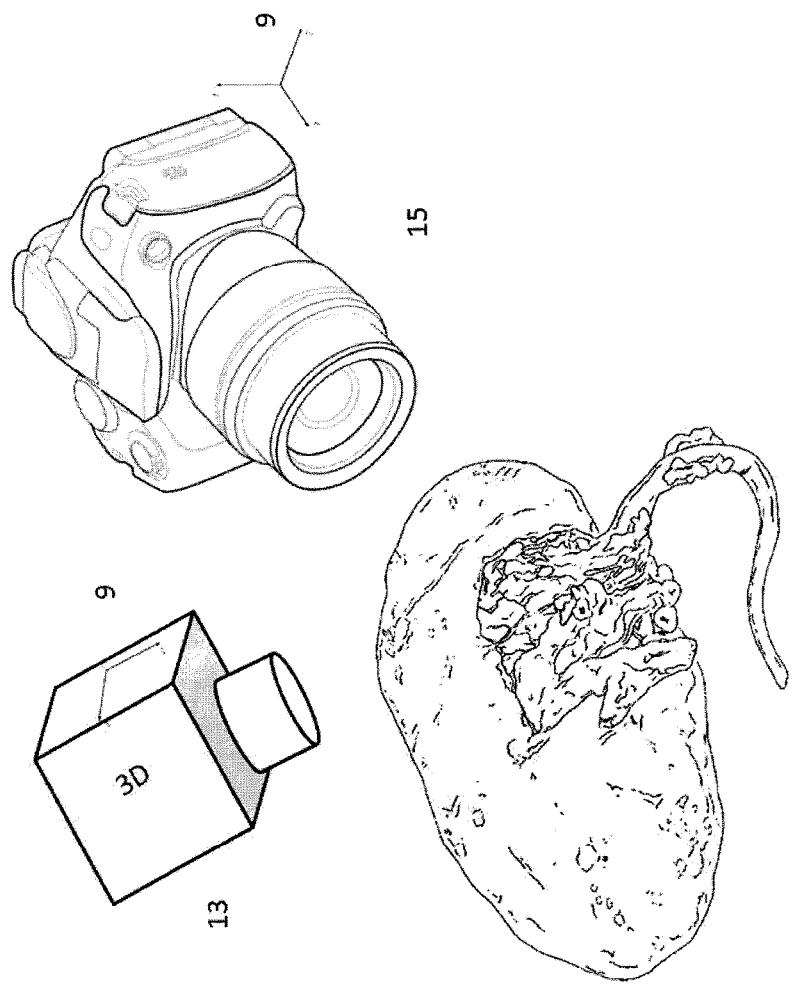
FIG. 6 illustrates the extension of the baseline of a stereoscopic camera arrangement for depth-sensing.

FIG. 6 illustrates an exemplary coordinate system 9 of a 3D camera 13 and an optical camera 15. The coordinate system 9 provided location coordinates that can be used in image correction process.

Figure 7:
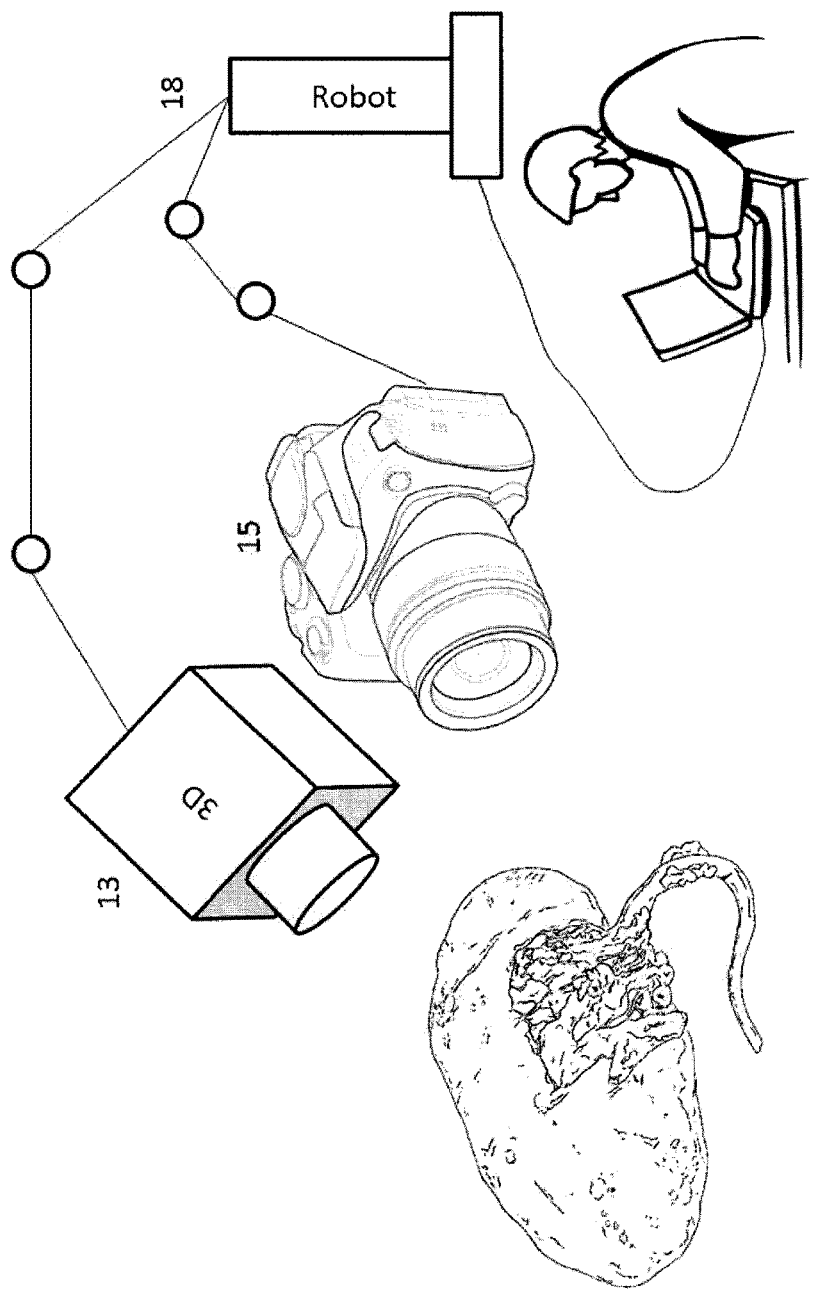
FIG. 7 illustrates an embodiment wherein the imagers and light source are controlled by a robot connected to the image processing workstation.
Figure 8:
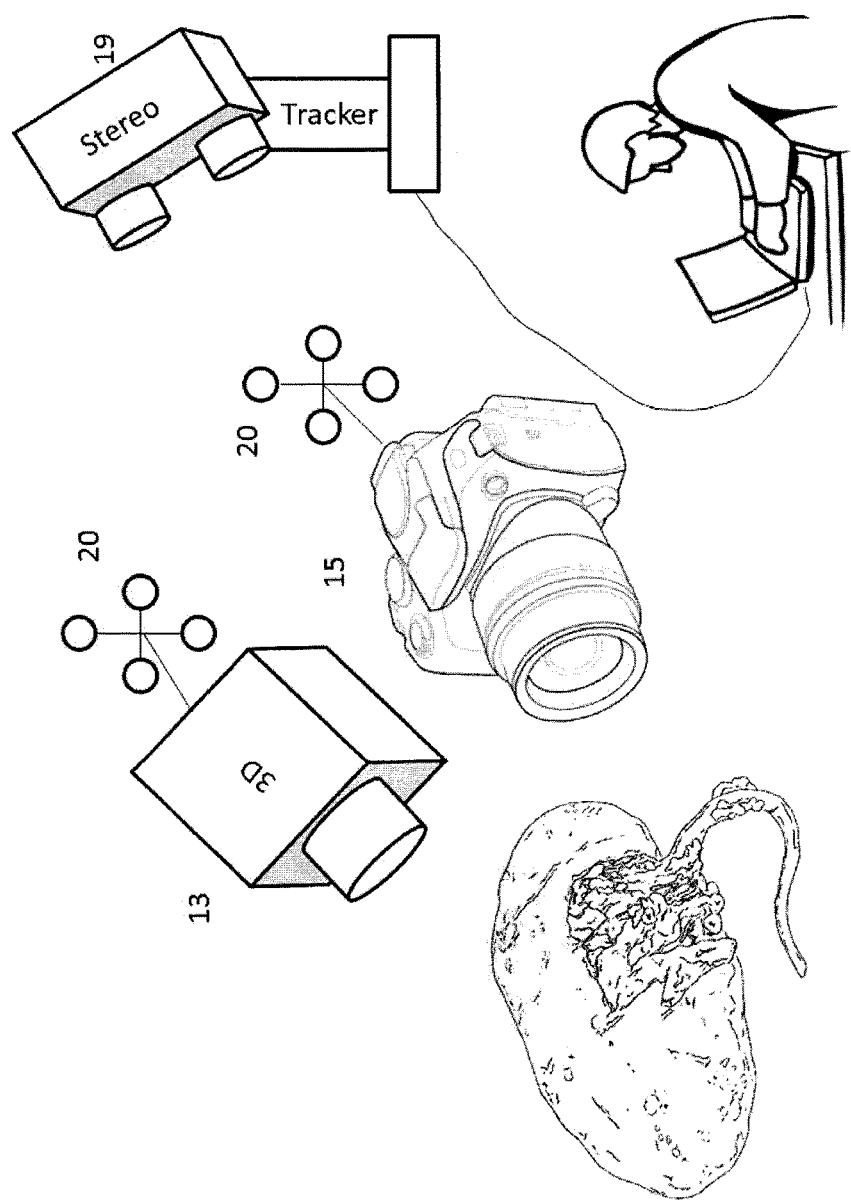
FIG. 8 illustrates an embodiment wherein the imagers and light source are tracked to determine position and orientation, and navigated by the workstation.

In another embodiment, shown in FIGS. 7 and 8, the system is configured for external use. FIG. 7 illustrates a robot 18 controlling each of the 3D camera 13 and the optical 15 camera 15. FIG. 8 illustrates a tracker 19 which looks at markers 20 to determine the position and orientation of the 3D camera 13 and optical camera 15.

The camera may be a plurality of optical cameras 15 available to the operator, and the depth sensing circuitry may be any sensor which can determine depth at points in the scene of interest. The cameras may be registered to one another via a calibration routine, position sensing or robot 18 controls. They may also be initially unregistered, and subsequently their image correlation and registration computed from features in their respective images. The illuminating light 14 may be rigidly linked to the camera or tracked by the system via a separate tracker 19. This provides a way to adjust the position of light used for camera exposure separately from the camera position. This feature may help image certain regions more closely when it is not feasible or desirable to change the camera position.

A surgeon may interact with the displayed images through a user interface that includes an input device (computer mouse, keyboard, microphone, buttons, joystick, touch screen, gesture control, etc.) to select various features and options. The surgeon can optionally switch between two-dimensional and three-dimensional views or can visualize them side by side on displays. The surgeon may use the user interface to change views, to change distortion 4 (in FIG. 1) or deformation model 5 (in FIG. 1) parameters, to rotate, scale, or translate 3D views, or to make other parameter changes that influences the display shown on monitors.

In the event that the final corrected images are not satisfactory, the system may suggest alternate locations for each of the optical camera, the depth sensors, and the illuminating light source. For example, in areas of high light saturation, the 3D depth sensor may not provide good depth information. In this case the system may suggest a different location or intensity of light for subsequent image capture sequences. The system may automatically command the optical camera, the depth sensors and the light source to the desired position in the case of a robotic 18 (in FIG. 7) embodiment or it may offer navigational guidance in the case of a tracked-tool embodiment. The new position for each component will be chosen to minimize the predicted distortion across a region of interest. The system may also offer a new set of intrinsic and extrinsic camera parameters, and a new position, orientation, and intensity for a plurality of illuminating lights.

The inclusion of a multitude of varying cameras aids the system's versatility. With each camera and imaging scenario, a new distortion model is generated. In the event that a processed image cannot be improved by repositioning the first user-selected camera, the system may calculate possibilities based on other cameras and/or other camera parameters and suggest a replacement.

Figure 14:
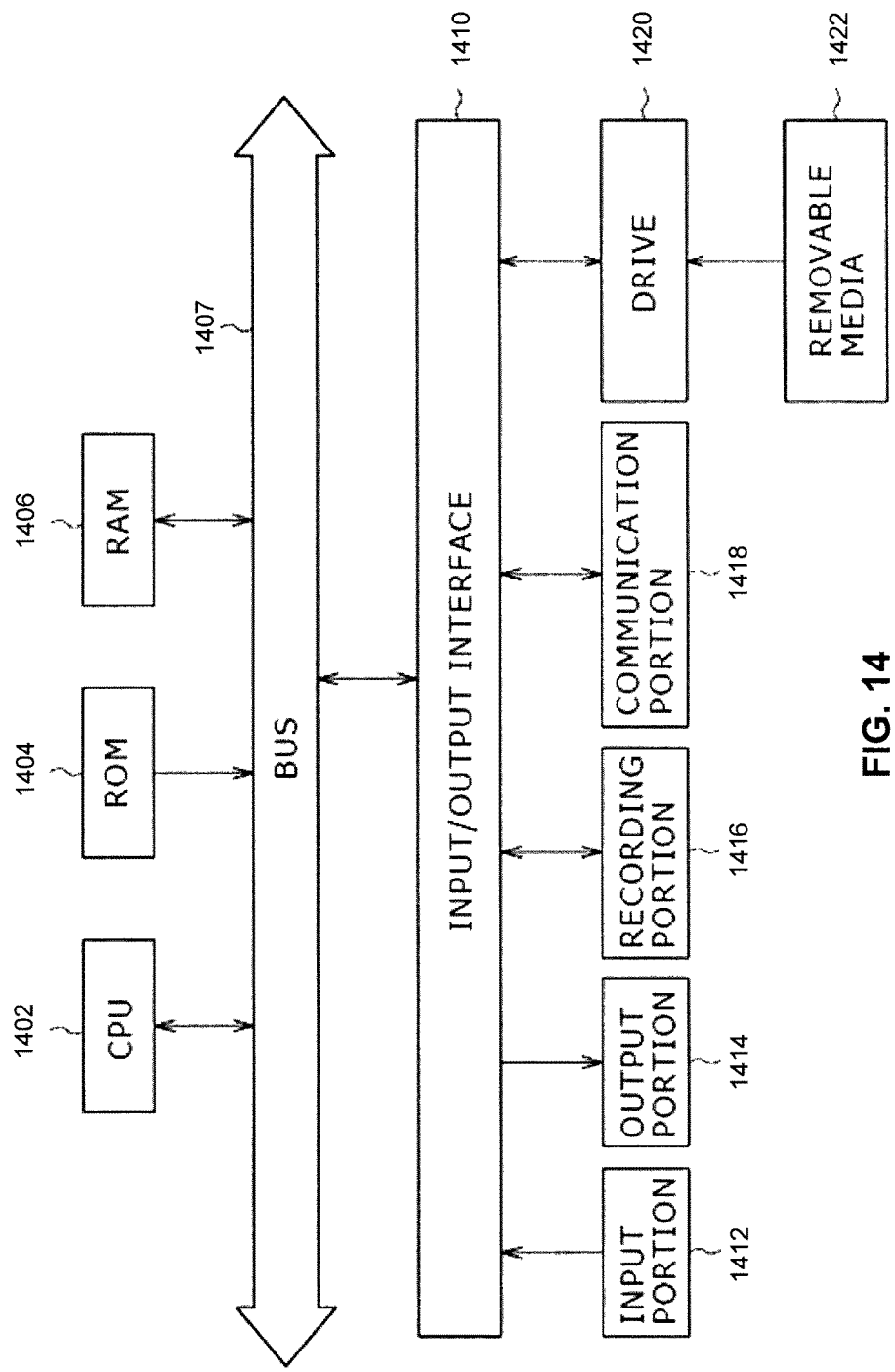
FIG. 14 illustrates a block diagram showing an example of a hardware configuration of a special purpose computer according to the present embodiments.

FIG. 14 illustrates a block diagram showing an example of a hardware configuration of a computer that is configured to implement one or more of the various processes described above. For example, in certain embodiments, the computer is configured to control the robot or tracer, imaging system position and orientation, and to implement the procedures 100 and 300. Moreover, the computer can be programmed to be more than a general purpose computer, for instance, the computer after executing the specific programming is transformed into a particular machine which implements a medical image processing system.

As illustrated in FIG. 14, the computer includes a central processing unit (CPU) 1402, read only memory (ROM) 1404, and a random access memory (RAM) 1406 interconnected to each other via one or more buses 1407. The one or more buses 1407 are further connected with an input-output interface 1410. The input-output interface 1410 is connected with an input portion 1412 formed by a keyboard, a mouse, a microphone, remote controller, touch screen, camera, sensors, etc. The input-output interface 1410 is also connected to: an output portion 1414 formed by an audio interface, video interface, display interface, speaker, etc.; a recording portion 1416 formed by a hard disk, a non-volatile memory, database etc.; a communication portion 1418 formed by a network interface, modem, USB interface, fire wire interface, etc.; and a drive 1420 for driving removable media 1422 such as a magnetic disk, an optical disk, a magneto-optical disk, a semiconductor memory, etc.

The input portion 1412 is connected to a laparoscope 12, an endoscope, a camera 15, a light source 14, depth sensing devices such as 3D camera 13 or light-field camera 16, and optical cameras 15. The inputs received from the input devices can be stored in the recording portion for further processing. The processing is performed according to the process 100 or 300 implemented in the recoding portion 1416 such as a hard disk. The images that are output of the processing are then displayed via the output portion 1414, which is connected to a display screen. These images can also be stored via a recording portion 1416 to a database or hard disk. Further the images can be transmitted to a qualified operator via a communication portion 1418 such internet, or USB. The operator can make further process the information on another computer or interaction with a computer or devices such as a robot 18 connected to the network.

According to one embodiment, the CPU 1402 loads a program stored in the recording portion 1416 into the RAM 1406 via the input-output interface 1410 and the bus 1407, and then executes a program configured to implement the present disclosure such as providing the functionality of the one or combination of the elements of the procedure 100 and 300. The recording portion 1416 is for example a non-transitory computer-readable storage medium. It is noted that the term "non-transitory" is a limitation of the medium itself (i.e., tangible, not a signal) as opposed to a limitation on data storage persistency (e.g., RAM vs. ROM).

Figure 15:
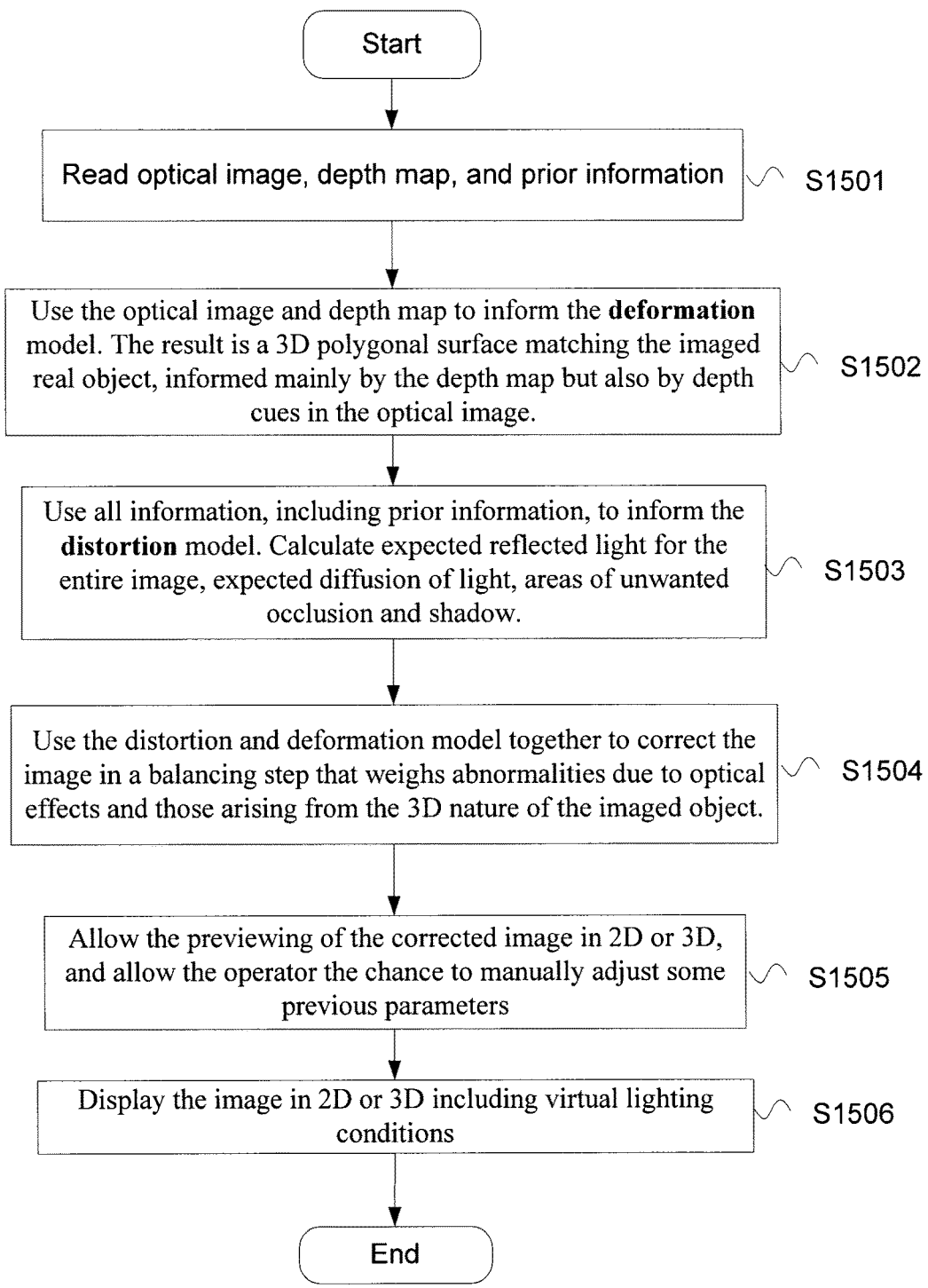
FIG. 15 illustrates an exemplary flow diagram.

Referring to FIG. 15, the 3D image correction method is summarized. The process starts when an object is configured and the cameras are in place. In step S1501, the prior information, depth map and optical image of the object are read into a system. In step S1502, the optical image and depth map are used to inform a deformation model. The deformation model outputs a 3D polygonal surface matching the image of the real object. The information required is mainly obtained from the depth map and by using depth cues in the optical image. In step S1503, all the information, including prior information is used to inform the distortion model. The distortion model includes calculation of expected reflected light for an entire image, expected diffusion of light, areas of unwanted occlusion and shadow. In step S1504, results from the distortion and deformation model are used simultaneously to correct the image in a balancing step that weighs abnormalities due to optical effects and those arising from the 3D nature of the imaged object. In step S1505, the preview of the corrected image in 2D or 3D is made available and allows the operator to manually adjust some previous parameters. The parameter adjustment may also be done automatically. In step S1506, the image is displayed in 2D or 3D and includes virtual lighting conditions.

According to one embodiment there is described a method for correcting captured images that includes recording prior knowledge, acquiring optical images, acquiring depth maps, registering the optical images and depth maps, generating distorted images using a distortion model to predict distortion within the optical images and depth maps, generating deformed images using a deformation model from the optical images, the depth maps and the prior knowledge, generating 3D mesh to cover the deformation model of the optical images and the depth maps, generating a corrected image using images resulting from the distortion model and the deformation model, and displaying the corrected image, the distorted images, the deformed images, and the first and the second set of images. The method may include a feedback step to acquire a new set of images at optimally determined locations. The method includes a feedback step that also includes a new, optimized position and orientation for an illuminating light. The method includes stitching together a plurality of optical images and depth maps to obtain a superior composite image. The method includes the distortion and/or deformation model taking into account the utilized light's wavelength and electric and magnetic field, the incidence angle and distance to the object, material composition of the object of interest, and any other parameters influencing diffuse or specular reflection. The method includes the distortion and/or deformation model taking into account prior images, including images from databases. The method includes the registration step being a rigid registration based on physically linked camera arrangements. The method includes the registration step being based on the images alone without prior knowledge of camera arrangement. The method includes the registration step being based on the information from a navigational tracker. The method includes an additional iterative step which adjusts the position and orientation of imagers and light sources automatically or in response to a guided instruction. The method includes optical image acquisition and depth image acquisition which is computer-suggested based on previous results.

According to one or more embodiments there is described a system and method for corrected imaging. The system and similarly the method describe an optical camera that captures at least one optical image of an area of interest, a depth sensor that captures at least one depth map of the area of interest, and circuitry configured to correlate depth information of the at least one depth map to the at least one optical image to generate a depth image, correct the at least one optical image by applying a model to address alteration in the respective at least one optical image, the model using information from the depth image, and output the corrected at least one optical image for display in 2D and/or as a 3D surface.

The system further including the optical camera and the depth sensor being positioned at the distal end of a laparoscopic tool. The system further including the circuitry being further configured to correct the at least one optical image by applying the model to address alteration in the respective at least one optical image, the model using information from the depth image and prior information including intensity and directionality of illumination in the area of interest. The system further including the model being a distortion model. The system further including the distortion model addressing alteration in the respective at least one optical image by generating a two dimensional image with additional information including at least one of expected luminance, spectral response, and depth at each pixel producing a three-dimensional surface and applying this information to determine at least one of an amount of extra light due to reflection, an adjustment in illumination due to surface orientation and occlusion, and an expected radiance and diffusion due to surface roughness. The system further including the model being a deformation model. The system further including the deformation model addressing alteration in the respective at least one optical image by segmenting the depth image into a multitude of polygons with a known size and orientation and grouping the polygons into discrete patches to generate a three-dimensional representation of a surface corresponding to the area of interest. The system further including the area of interest being a physiological portion of a medical patient. The system further including the optical camera being configured to capture multispectral or hyperspectral images. The system further including the depth sensor being a light field camera. The system further including the depth sensor including at least two stereo-vision cameras. The system further including the depth sensor utilizing a structured light. The system further including an adjustable light source being included and configured to illuminate an object at a particular angle and intensity. The system further including a baseline of the stereo-vision cameras being adjusted. The system further including the optical camera and the depth sensor being tracked by a navigational system. The system further including optical camera and the depth sensor being actuated by a robotic system.

A method for corrected imaging that includes capturing at least one optical image of an area of interest using an optical camera, capturing at least one depth map of the area of interest using a depth sensor, correlating depth information of the at least one depth map to the at least one optical image to generate a depth image, correcting the at least one optical image by applying a model to address alteration in the respective at least one optical image, the model using information from at least one of the depth image, optical image, and prior information, and outputting the corrected at least one optical image for display in 2D and/or as a 3D surface.

The method for corrected imaging in which the optical camera and the depth sensor are positioned at the distal end of a laparoscopic tool. The method for corrected imaging further includes correcting the at least one optical image by applying the model to address alteration in the respective at least one optical image, the model using information from the depth image and prior information including intensity and directionality of illumination in the area of interest The method for corrected imaging in which the model is a distortion model. The method for corrected imaging in which the correcting further includes applying the distortion model to address alteration in the respective at least one optical image by generating a two dimensional image with additional information, including at least one of expected luminance, spectral response, and depth at each pixel producing a three-dimensional surface and applying the three-dimensional surface to determine at least one of an amount of extra light due to reflection, an adjustment in illumination due to surface orientation and occlusion, and an expected radiance and diffusion due to surface roughness. The method for corrected imaging in which the model is a deformation model. The method for corrected imaging in which the correcting further includes applying the deformation model to address alteration in the respective at least one optical image by segmenting the depth image into a multitude of polygons with a known size and orientation and grouping the polygons into discrete patches to generate a three-dimensional representation of a surface corresponding to the area of interest.

A non-transitory computer readable medium having stored thereon a program that when executed by a computer causes the computer to implement a method for corrected imaging that includes capturing at least one optical image of an area of interest using an optical camera, capturing at least one depth map of the area of interest using a depth sensor, correlating depth information of the at least one depth map to the at least one optical image to generate a depth image, correcting the at least one optical image by applying a model to address alteration in the respective at least one optical image, the model using information from the depth image, and outputting the corrected at least one optical image for display in 2D and/or as a 3D surface.

What is claimed is:
1. A system for corrected imaging, comprising:
an optical camera that captures at least one optical image of an area of interest;
a depth sensor that captures at least one depth map of the area of interest; and
circuitry configured to
associate depth information of the at least one depth map to the at least one optical image to generate a depth image, correct the at least one optical image by applying a distortion model and a deformation model to address alteration in the respective at least one optical image due to undesired effects of distortion caused by imaging abnormalities and image artifacts caused by imaging of a three-dimensional deformed surface, the distortion model using information from the depth image, optical image information associated with the captured at least one optical image, and prior information, the deformation model using the information from the depth image and the optical image information, but not the prior information, and the prior information including intensity and directionality of illumination in the area of interest, and output the corrected at least one optical image for display in two-dimensions (2D) and/or in three-dimensions (3D).

2. The system for corrected imaging according to claim 1, wherein the optical camera and the depth sensor are positioned at the distal end of a laparoscopic tool.

3. The system for corrected imaging according to claim 1, wherein the circuitry is further configured to weigh the correction applied by the distortion model against the correction applied by the deformation model, output a preview image, and reapply, based on a determination of quality acceptability of the preview image, correction of the at least one optical image using at least one new system parameter, the at least one new system parameter including a change to one or more of optical image-sensing circuitry, depth-sensing circuitry, camera or depth sensing sensor position, and camera or depth-sensor orientation.

4. The system for corrected imaging according to claim 1, wherein the distortion model addresses alteration in the respective at least one optical image based on a two dimensional image with additional information, including at least one of expected luminance, spectral response, and depth at each pixel producing a three-dimensional surface and applying this information to determine at least one of an amount of extra light due to reflection, an adjustment in illumination due to surface orientation and occlusion, and an expected radiance and diffusion due to surface roughness.

5. The system for corrected imaging according to claim 1, wherein the deformation model addresses alteration in the respective at least one optical image by segmenting the depth image into a multitude of polygons with a known size and orientation and grouping the polygons into discrete patches to generate a three-dimensional representation of a surface corresponding to the area of interest.

6. The system for corrected imaging according to claim 1, wherein the area of interest is a physiological portion of a medical patient.

7. The system for corrected imaging according to claim 1, wherein the optical camera is configured to capture multi-spectral or hyperspectral images.

8. The system for corrected imaging according to claim 1, wherein the depth sensor is a light field camera.

9. The system for corrected imaging according to claim 1, wherein the depth sensor includes at least two stereo-vision cameras.

10. The system for corrected imaging according to claim 9, wherein a baseline of the stereo-vision cameras is adjustable.

11. The system for corrected imaging according to claim 1, wherein the depth sensor utilizes a structured light.

12. The system for corrected imaging according to claim 1, further comprising an adjustable light source configured to illuminate an object at a particular angle and intensity.

13. The system for corrected imaging according to claim 1, wherein the optical camera and the depth sensor are tracked by a navigational system.

14. The system for corrected imaging according to claim 1, wherein the optical camera and the depth sensor are actuated by a robotic system.

15. A method for corrected imaging, comprising:

capturing at least one optical image of an area of interest using an optical camera;

capturing at least one depth map of the area of interest using a depth sensor;

associating depth information of the at least one depth map to the at least one optical image to generate a depth image;

correcting the at least one optical image by applying a distortion model and a deformation model to address alteration in the respective at least one optical image due to undesired effects of distortion caused by imaging abnormalities and image artifacts caused by imaging of a three-dimensional deformed surface, the distortion model using information from the depth image, optical image information associated with the captured at least one optical image, and prior information, the deformation model using the information from the depth image and the optical image information, but not the prior information, and the prior information including intensity and directionality of illumination in the area of interest; and outputting the corrected at least one optical image for display in 2D and/or as a 3D surface.

16. The method for corrected imaging according to claim 15, wherein the optical camera and the depth sensor are positioned at the distal end of a laparoscopic tool.

17. The method for corrected imaging according to claim 15, further comprising:

weighting the correction applied by the distortion model against the correction applied by the deformation model;

outputting a preview image; and reapplying, based on a determination of quality acceptability of the preview image, correction of the at least one optical image using at least one new system parameter, the at least one new system parameter including a change to one or more of optical image-sensing circuitry, depth-sensing circuitry, camera or depth sensing sensor position, and camera or depth-sensor orientation.

18. The method for corrected imaging according to claim 15, wherein said correcting further comprises: applying the distortion model to address alteration in the respective at least one optical image based on a two dimensional image with additional information, including at least one of expected luminance, spectral response, and depth at each pixel producing a three-dimensional surface and applying the three-dimensional surface to determine at least one of an amount of extra light due to reflection, an adjustment in illumination due to surface orientation and occlusion, and an expected radiance and diffusion due to surface roughness.

19. The method for corrected imaging according to claim 15, wherein said correcting applied by the deformation model further comprises:

applying the deformation model to address alteration in the respective at least one optical image by segmenting the depth image into a multitude of polygons with a known size and orientation and grouping the polygons into discrete patches to generate a three-dimensional representation of a surface corresponding to the area of interest.

20. A non-transitory computer readable medium having stored thereon a program that when executed by a computer causes the computer to implement a method for corrected imaging, comprising:

capturing at least one optical image of an area of interest using an optical camera;

capturing at least one depth map of the area of interest using a depth sensor;

associating depth information of the at least one depth map to the at least one optical image to generate a depth image;

correcting the at least one optical image by applying a distortion model and a deformation model to address alteration in the respective at least one optical image due to undesired effects of distortion caused by imaging abnormalities and image artifacts caused by imaging of a three-dimensional deformed surface, the distortion model using information from the depth image, optical image information associated with the captured at least one optical image, and prior information, the deformation model using the information from the depth image and the optical image information, but not the prior information, and the prior information including intensity and directionality of illumination in the area of interest; and outputting the corrected at least one optical image for display in 2D and/or as a 3D surface.

* * * * *